United States Patent [19]
Boyle et al.

[11] 3,962,237
[45] June 8, 1976

[54] 1 (H)-1,2,4-TRIAZOLE DERIVATIVES

[75] Inventors: John Terence Arnott Boyle; John Christopher Saunders, both of Maidenhead, England

[73] Assignee: John Wyeth & Brother Limited, Maidenhead, England

[22] Filed: Feb. 6, 1975

[21] Appl. No.: 547,669

[30] Foreign Application Priority Data
Feb. 11, 1974  United Kingdom................ 6139/74

[52] U.S. Cl.................... 260/247.1 M; 260/293.69; 260/308 R; 424/248; 424/267; 424/269
[51] Int. Cl.²........................................ C07D 249/08
[58] Field of Search............... 260/247.1 M, 293.69, 260/308 R; 424/248, 267, 269

[56] References Cited
UNITED STATES PATENTS 3,689,501   9/1972   Weaver et al.................. 260/308 R
3,867,395   2/1975   Seidel et al. ................... 260/308 R FOREIGN PATENTS OR APPLICATIONS
41-3096   9/1967   Japan............................. 260/308 R

*Primary Examiner*—Robert Gerstl
*Assistant Examiner*—Michael Shippen
*Attorney, Agent, or Firm*—Richard K. Jackson

[57] ABSTRACT

This invention relates to compounds having the formula:

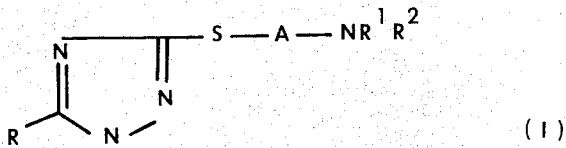

(1)

and the pharmaceutically acceptable acid addition salts thereof, wherein R represents a phenyl or substituted phenyl radical in which said substituent is halogen, lower alkyl, lower alkoxy, nitro or trihalo lower alkyl; A represents a lower alkylene radical; and $R^1$ and $R^2$ independently represents hydrogen or lower alkyl; or $R^1$ and $R^2$ together with the nitrogen to which they are attached represent a heterocyclic ring selected from pyrrolidino, piperidino or morpholino; which inhibit blood platelet aggregation.

7 Claims, No Drawings

1 (H)-1,2,4-TRIAZOLE DERIVATIVES

This invention relates to novel triazole derivatives, to processes for their preparation, and to pharmaceutical compositions containing them.

More particularly this invention provides novel triazole derivatives having the formula:

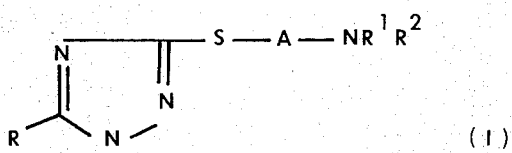

(I)

wherein R represents a phenyl or substituted phenyl radical in which said substituent is halogen, lower alkyl, lower alkoxy, nitro or trihalo lower alkyl; A represents a lower alkylene radical; and $R^1$ and $R^2$ independently represent hydrogen or lower alkyl; or $R^1$ and $R^2$ together with the nitrogen to which they are attached represent a heterocyclic ring selected from pyrrolidion, piperidino or morpholino; and the pharmaceutically acceptable acid addition salts thereof.

The term "lower alkylene" as used herein signifies that the alkylene chain contains from 1 to 6 carbon atoms and includes both straight and branched chains. By the term "lower alkyl" as used herein is meant an alkyl radical of 1 to 6 carbon atoms.

Examples of substituted phenyl radicals for R are fluorophenyl, clorophenyl, bromophenyl, tolyl, ethylphenyl, propylphenyl, methoxyphenyl, ethoxyphenyl, propoxyphenyl nitrophenyl, and trifluoromethylphenyl.

Preferably R is phenyl, or monohalophenyl, e.g. p-chlorophenyl. Examples of straight chain A radicals are methylene, ethylene, propylene and butylene; examples of branched chain A radicals are

Preferably A is propylene. Examples of $R^1$ are hydrogen, methyl, ethyl, n-propyl, iso-propyl, and n-butyl. Preferably $R^1$ is methyl. Examples of $R^2$ are the same as for $R^1$. A preferred group for $R^2$ is methyl. The acid addition salts of the compounds of formula I include salts formed with inorganic acids such as hydrochlorides, hydrobromides, sulphates, nitrates, phosphates, or salts formed with organic acids such as acetates, citrates, tartrates, maleates, fumarates, formates and sulphonates.

The novel compounds provided by the present invention possess pharmacological activity, in particular inhibition of blood platelet aggregation, and may also be intermediates for other compounds of the invention. Compounds of formula (I) which particularly inhibit blood platelet aggregation are those wherein $R^1$ and $R^2$ are both lower alkyl or a heterocyclic ring as hereinbefore defined. The compounds were tested for their effect on blood platelets by a method based on that by Born and Cross, J.Physiol., 168, pps 178–195 (1963). The results are expressed as the minimum concentration effective, i.e. the concentration which gives 50 percent inhibition of the induced aggregation. The compounds of this invention inhibit blood platelet aggregation and are useful in the treatment of vascular disease, particularly in the treatment or prevention of vascular thrombosis in mammals.

Representative of the activity of the compounds of this invention is 3-(dimethylaminopropylthio)-5-p-chlorophenyl-1(H)-1,2,4-triazole which, as the dihydrochloride salt, exhibited 50% inhibition at a concentration of $2.2 \times 10^{-4}$M in the above mentioned test in vitro.

Compounds of formula (I) may also exhibit other pharmacological activities. For example, 3-(dimethylaminopropylthio)-5-p-chlorophenyl-1(H)-1,2,4-triazole, dihydrochloride, also shows antihypertensive, antitrichomonal and some CNS activity, e.g. antidepressant, in standard pharmacological tests.

It will be apparent to those skilled in the art that compounds of formula (I), where the 1,2,4-triazole ring carries a hydrogen atom, may exist in different tautomeric structures. Thus the 1,2,4-triazole ring may have the formula:

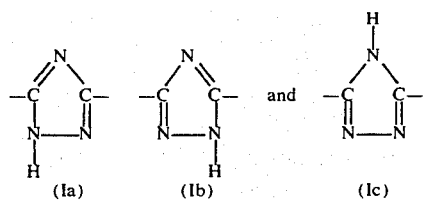

(Ia)  (Ib)  (Ic)

Where compounds of the invention may exist in more than one tautomeric structure it is to be understood that all tautomeric structures are intended. However, for the compounds of this invention tautomers (Ia) and (Ib) would be expected to predominate.

The present invention further provides processes for preparing the compounds of formula (I). A first general method comprises reacting a compound of formula:

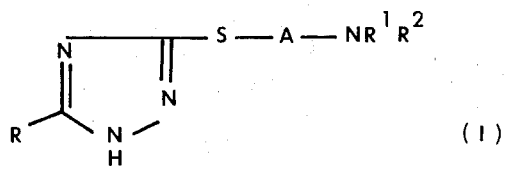

(I)

wherein R is as defined above, with a compound of formula;

X— A —NR¹R²  (III)

wherein A, $R^1$ and $R^2$ are as defined above and X is a halogen atom, e.g. chlorine, bromine, or iodine or an equivalent replaceable atom or radical such as an organic sulphonyloxy radical, e.g. p-toluenesulphonyloxy. Preferably X is chlorine or bromine. The reaction is conveniently carried out by heating; preferably in the pesence of base, such as an alkali metal hydroxide, e.g. KOH or NaOH; an alkali metal carbonate, e.g. $K_2CO_3$ or $Na_2CO_3$; or a tertiary amine.

A further process for preparing compounds of formula (I) in which $R^1$ is hydrogen and $R^2$ represents a normal or secondary lower alkyl radical, comprises reacting under reducing conditions a compound of formula (I) wherein $R^1$ and $R^2$ both represent hydrogen, with an aldehyde or ketone of formula:

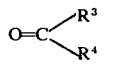
(IV)

wherein $R^3$ is hydrogen, methyl or ethyl and $R^4$ is hydrogen or alkyl of 1 to 3 carbon atoms which may be branched or straight chain. Examples of suitable reducing conditions are those provided by the presence of a hydrogenation catalyst, for example platinum oxide, hydrogen and an excess of carbonyl compound. Other catalysts include nickel or palladium, e.g. palladium charcoal. Alternatively a hydride transfer agent such as an alkali metal borohydride, e.g. sodium borohydride may be used.

Yet a further process for preparing compounds of formula (I) wherein $R^1$ represents methyl and $R^2$ represents lower alkyl, comprises reacting a compound of formula I, wherein $R^1$ represents hydrogen and $R^2$ represents lower alkyl, with formaldehyde and formic acid. Such a reaction may be carried out under Eschweiler-Clarke reaction conditions. Similarly compounds of formula I wherein $R^1$ and $R^2$ both represent methyl may also be prepared by reacting a compound of formula I wherein $R^1$ and $R^2$ both represent hydrogen, with formaldehyde and formic acid. Again Eschweiler-Clarke reaction conditions may be used. In connection with the Eschweiler-Clarke reaction referred to above and conditions under which it may be carried out, reference may be made to the literature, in particular, to a paper by H. T. Clarke et al. J. Amer. Chem. Soc., 55, 4571 (1933), and to a review by Moore, Organic Reactions, 5, 301(1949).

Some of the compounds of formula (II) used as starting materials for preparing compounds of formula (I) as described above are known compounds and reference may be made to the literature for methods for preparing them, e.g. E. Hoggarth, J. Chem. Soc., 1160 (1949). Such methods are applicable to the preparation of the other compounds of formula (II) which are novel.

However, a further aspect of the present invention is the provision of a novel process for preparing the compounds of formula (II), which comprises reacting a compound of formula (V)

(V)

wherein R is as hereinbefore defined and X is a halogen, preferably chlorine or bromine, with thiosemicarbazide. The reaction is preferably carried out in the presence of a base, for example an alkali metal hydroxide, e.g. NaOH or KOH. This reaction may be brought to completion by heating.

It is believed that the above mentioned reaction proceeds via an intermediate of formula:

(VI)

which then cyclises to give the compounds of formula (II).

This invention therefore includes a process where a compound of formula (II) is prepared by cyclising a compound of formula (VI).

In preparing the compound of formula (II) from the compounds of formula (V) and thiosemicarbazide it is preferred to mix the reactants at a temperature at or below room temperature to form a compound of formula (VI). This is preferably cyclised by heating.

Yet a further aspect of this invention provides a pharmaceutical composition comprising a compound of the formula (I) as hereinbefore defined or a pharmaceutically acceptable acid addition salt thereof, together with a pharmaceutically acceptable carrier. The carrier for the composition can be solid, liquid or mixed solid-liquid, and any suitable carrier known in the art can be used. The particular carrier chosen will depend on the actual compound, the desired method of administration and standard pharmaceutical practice. The compositions may be in the form of, for example, tablets, capsules or solutions.

The proportion of carrier to active compound will be determined by the solubility and chemical nature of the carrier, the chosen route of administration and standard pharmaceutical practice. The active compounds may, for example, be administered orally or parenterally. For example, they may be administered orally in unit does form, for example as tablets, capsules and the like. They may also be administered orally in the form of solutions or they may be injected parenterally. For parenteral administration they may be used in the form of a sterile solution or suspension containing other solutes, for example enough saline or glucose to make the solution isotonic.

The dosage of the present agents will vary with the form of administration and the particular compound chosen. Furthermore, it will vary with the particular subject under treatment. Generally, treatment is initiated with a small dosage substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects.

The following non-limiting Examples illustrate the invention. Examples 1, 3 and 6(a) to 6(f) concern the preparation of starting materials by the novel process of this invention. Examples 2, 4, 5, 7(a) to 7(e) and 8(a) to 8(f) concern the preparation of novel compounds of this invention.

EXAMPLE 1

3-Mercapto-5-phenyl-1(H)-1,2,4-triazole

To a cooled solution of thiosemicarbazide (91.14 g, 1.0 moles) in 2N NaOH (1.0 liters) was added dropwise benzoyl chloride (140.6 g., 1.0 moles) and the solution was stirred for 2 hours. The solution as then refluxed for 3 hours, and on cooling and standing a crystalline solid separated. Most of this solid dissolved again on addition of 10N NaOH (100 mls.) and a small amount of yellow material was filtered from the basic solution. Concentrated HCl was added to the filtrate to bring the solution to pH7 whereupon the title compound separated as a white solid and was filtered off (190 gms). This compound was used, without further purification, as described in Examples 2 and 5. However, a small amount was recrystallised from ethanol/water for analytical purposes, m.p. 254°–256°C.

(ANALYSIS: Found: C, 53.87; H, 3.91; N, 23.34%. $C_8H_7N_3S$ requires: C, 54.21; H, 3.98; N, 23.71%).

EXAMPLE 2

3-(2-Diethylaminoethylthio)-5-phenyl-1(H)-1,2,4-triazole

3-Mercapto-5-phenyl-1(H)-1,2,4-triazole (8.86 g, 0.05 moles), prepared as described in the foregoing Example, and 2-diethylaminoethyl chloride hydrochloride (8.61 g, 0.05 moles) were refluxed together for 2 hours in 75 mls. of 2N NaOH with 75 mls. of ethanol. On cooling the solution was filtered and the ethanol removed on a rotary evaporator. The alkaline solution was extracted with ether (2 × 100 mls), and the excess ether was removed from the aqueous fraction by boiling. On cooling the aqueous fraction was brought to pH8 and a gum separated. This mixture was then extracted first with ethyl acetate, then with 2N HCl, washed with ethyl acetate and the solution basified to pH8 using potassium carbonate. The compound was again extracted into ethyl acetate, washed with water and dried using anhydrous magnesium sulphate. To this solution HCl/ethanol was added and then sufficient ethanol to dissolve the precipitate on heating and diethyl ether was added to bring the solution to the brink of crystallisation. On cooling the title compound crystallised out (7.5 gms) as the monohydrochloride quaterhydrate, m.p. 139°–141°C.

ANALYSIS: Found: C, 53.00; H, 6.66; N, 17.49% $C_{14}H_{20}N_4S \cdot HCl \cdot \frac{1}{4}H_2O$ requires: C, 53.00; H, 6.83; N, 17.65%).

EXAMPLE 3

3-Mercapto-5-(p-chlorophenyl)-1(H)-1,2,4-triazole

To a cooled solution of thiosemicarbazide (45.57 g, 0.5 moles) in 2N NaOH (1.0 liters) was added dropwise p-chlorobenzoyl chloride (100 g, 0.57 moles) and the solution was stirred for 2 hours in the cold. The solution was then refluxed for 3 hours and, on cooling, was filtered. Concentrated HCl was added to the filtrate to bring the solution to pH 8 whereupon the title compound separated and was filtered off. The product (122.3 g) was then washed and dried for use as described in the following Example.

EXAMPLE 4

3-(3-Dimethylaminopropylthio)-5-(p-chlorophenyl)-1-(H)-1,2,4-triazole

3-Mercapto-5-(p-chlorophenyl)-1(H)-1,2,4-triazole (10.59 g, 0.05 moles), prepared as described in Example 3, and 3-dimethylaminopropyl chloride hydrochloride (7.91 g, 0.05 moles), were refluxed together in 75 mls. of 2N NaOH with 75 mls. of 95% ethanol. On cooling, the reaction mixture was filtered and the ethanol removed on a rotary evaporator. The mixture was then filtered again and extracted with ether (2 × 100 mls). During the extraction three layers were present, therefore, the middle oily layer and the aqueous layer were extracted together. This mixture of layers was then brought to pH8 by addition of 2N hydrochloric acid, extracted with ethyl acetate (2 × 100 mls), and the extract dried (MgSO₄). To this solution HCl/ethanol was added and a gelatinous precipitate appeared. The precipitate was filtered off and dried (8.70 g). recrystallisation from methanol/diisopropyl ether gave the title compound as the dihydrochloride salt m.p. 162°–166°C.

(ANALYSIS: Found: C, 42.61; H, 5.27; N, 15.15%. $C_{13}H_{17}N_4ClS \cdot 2HCl$ requires: C, 42.23; H, 5.18; N, 15.15%).

EXAMPLE 5

3-(2-[N-Morpholino]ethylthio)-5-phenyl-1(H)-1,2,4-triazole

3-Mercapto-5-phenyl-1(H)-1,2,4-triazole (8.86 g, 0.05 moles), prepared as described in Example 1, and 2-(N-morpholino)-ethyl chloride hydrochloride (9.305 g, 0.05 moles) were refluxed together in a mixture of 75 mls. of 2N NaOH with 75 mls. of 95% ethanol for 1½ hours. On cooling the solution was filtered and the ethanol removed under vacuum. On neutralising the solution an oil separated which crystallised after standing for several days. Filtration gave the title compound as a low-melting white solid (11.15 g).

(ANALYSIS: Found: C, 54.64; H, 6.36; N, 17.78%. $C_{14}H_{18}N_4OS \cdot H_2O$ requires: C, 54.53; H, 6.54; N, 18.17%).

The title compound was converted to its dihydrochloride salt by dissolving in acetone and adding HCl/ether whereupon the salt precipitated (10.15 g) m.p. 210°–214°C.

(ANALYSIS: Found: C, 46.33; H, 5.56; N, 15.47%. $C_{14}H_{18}N_4OS \cdot 2HCl$ requires: C, 46.28; H, 5.55; N, 15.42%).

EXAMPLES 6(a) TO 6(f)

Using an analogous procedure to that described in Example 1 the following compounds:

(a) p-Toluoyl chloride,
(b) m-Toluoyl chloride,
(c) m-Chlorobenzoyl chloride,
(d) p-Methoxybenzoyl chloride,
(e) m-Nitrobenzoyl chloride,
(f) p-Trifluoromethyl benzoyl bromide may be reacted separately with thiosemicarbazide to give:

(a) 3-Mercapto-5-(p-tolyl)-1(H)-1,2,4-triazole,
(b) 3-Mercapto-5-(m-tolyl)-1(H)-1,2,4-triazole,
(c) 3-Mercapto-5-(m-chlorophenyl)-1(H)-1,2,4-triazole,
(d) 3-Mercapto-5-(p-methoxyphenyl)-1(H)-1,2,4-triazole,
(e) 3-Mercapto-5-(m-nitrophenyl)-1(H)-1,2,4-triazole,
(f) 3-Mercapto-5-(p-trifluoromethylphenyl)-1(H)-1,2,4-triazole
respectively.

EXAMPLE 7(a) TO 7(e)

Using an analogous procedure to that described in Example 4 the following compounds:

(a) 2-[Dimethylamino]ethyl chloride,
(b) 4-[Dimethylamino]butyl chloride,
(c) 3-[Di-n-propylamino]propyl chloride,
(d) 3-[N-Pyrrolidino]propyl chloride,
(e) 2-methyl-3-[Dimethylamino]propyl chloride may be reacted separately with 3-mercapto-5-(p-chlorophenyl)-1(H)-1,2,4-triazole to give:

(a) 3-(2-[Dimethylamino]ethylthio)-5-(p-chlorophenyl)-1(H)-1,2,4-triazole,
(b) 3-(4-[Dimethylamino]butylthio)-5-(p-chlorophenyl)-1(H)-1,2,4-triazole,
(c) 3-(3-[Di-n-propylamino]propylthio)-5-(p-chlorophenyl)-1(H)-1,2,4-triazole,
(d) 3-(3-[N-Pyrrolidino]propylthio)-5-(p-chlorophenyl)-1(H)-1,2,4-triazole,
(e) 3-(2-Methyl-3-[dimethylamino]propylthio)-5-(p-chlorophenyl)-1(H)-1,2,4-triazole, respectively.

EXAMPLES 8(a) TO 8(f)

Using an analogous procedure to that described in Example 4 the following compounds, prepared according to Example 6:

(a) 3-Mercapto-5-(p-tolyl)-1(H)-1,2,4-triazole,
(b) 3-Mercapto-5-(m-tolyl)-1(H)-1,2,4-triazole,
(c) 3-Mercapto-5-(m-chlorophenyl)-1(H)-1,2,4-triazole,
(d) 3-Mercapto-5-(p-methoxyphenyl)-1(H)-1,2,4-triazole,
(e) 3-Mercapto-5-(m-nitrophenyl)-1(H)-1,2,4-triazole,
(f) 3-Mercapto-5-(p-trifluoromethylphenyl)-1(H)-1,2,4-triazole, may be reacted separately with 3-[dimethylamino]propyl chloride to give:

(a) 3-(3-[Dimethylamino]propylthio)-5-(p-tolyl)-1(H)-1,2,4-triazole,
(b) 3-(3-[Dimethylamino]propylthio)-5-(m-tolyl)-1(H)-1,2,4-triazole,
(c) 3-(3-[Dimethylamino]propylthio)-5-(m-chlorophenyl)-1(H)-1,2,4-triazole,
(d) 3-(3-[Dimethylamino]propylthio)-5-(p-methoxyphenyl)-1(H)-1,2,4-triazole,
(e) 3-(3-[Dimethylamino]propylthio)-5m-nitrophenyl)-1(H)-1,2,4-triazole,
(f) 3-(3-[Dimethylamino]propylthio)-5-(p-trifluoromethylphenyl)-1(H)-1,2,4-triazole.

We claim:
1. A compound of the formula:

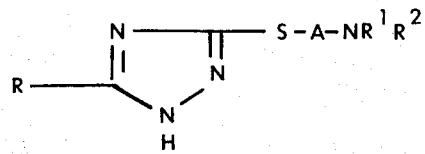

wherein,
R is phenyl or substituted phenyl in which said substituent is halo, lower alkyl, lower alkoxy, nitro or trihalo(lower)alkyl;
A is lower alkylene;
$R^1$ and $R^2$ are independently hydrogen or lower alkyl or, when taken together with the nitrogen atom to which they are attached, represent pyrrolidino, piperidino, or morpholino;
or a pharmaceutically acceptable acid addition salt thereof.

2. A compound as claimed in claim 1 wherein R represents phenyl or p-chlorophenyl.

3. A compound as claimed in claim 1 wherein A is propylene.

4. A compound as claimed in claim 1 wherein $R^1$ and $R^2$ both represent methyl.

5. A compound as claimed in claim 1, which is 3-(3-dimethylaminopropylthio)-5-(p-chlorophenyl)-1(H)-1,2,4-triazole or a pharmaceutically acceptable acid addition salt thereof.

6. A compound as claimed in claim 1 which is 3-(2-diethylaminoethylthio)-5-phenyl-1(H)-1,2,4-triazole or a pharmaceutically acceptable acid addition salt thereof.

7. A compound as claimed in claim 1 which is 3-(2-[N-morpholino]ethylthio)-5-phenyl-1(H)-1,2,4-triazole or a pharmaceutically acceptable acid addition salt thereof.

* * * * *

UNITED STATES PATENT OFFICE
CERTIFICATE OF CORRECTION

PATENT NO. : 3,962,237
DATED : June 8, 1976
INVENTOR(S) : John Terence Arnott Boyle
John Christopher Saunders It is certified that error appears in the above-identified patent and that said Letters Patent are hereby corrected as shown below:

Column 1 line 37 "chlorophenyl" is mis-spelled.

Column 2 lines 44 to 56 – the formula is incorrect it should be formula II as shown below:

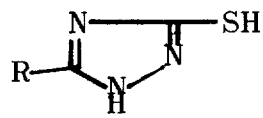

Column 4 line 33 "dose" is mis-spelt.
Column 5 lines 36 and 37 "quarterhydrate" is mis-spelt
Column 7 line 4 "Pyrrolidino" is mis-spelt.
Column 8 line 3 "-5m." should read "-5-(m".

Signed and Sealed this

Twelfth Day of October 1976

[SEAL]

Attest:

RUTH C. MASON
Attesting Officer

C. MARSHALL DANN
Commissioner of Patents and Trademarks